(12) United States Patent
Kao et al.

(10) Patent No.: US 6,375,622 B1
(45) Date of Patent: Apr. 23, 2002

(54) BRUSH-WRITING INSTRUMENTS FOR HEALTH AND THERAPY

(75) Inventors: Shang Ren Henry Kao; Ching Hui Goan, both of Hong Kong (HK)

(73) Assignee: The University of Hong Kong (HK)

( * ) Notice: Subject to any disclaimer, the term of this patent is extended or adjusted under 35 U.S.C. 154(b) by 0 days.

(21) Appl. No.: 09/616,801

(22) Filed: Jul. 14, 2000

(51) Int. Cl.[7] .................................................. A61B 5/00
(52) U.S. Cl. ..................... 600/485; 600/500; 600/504; 600/300; 600/301; 600/529; 600/549; 600/561; 600/587; 600/595
(58) Field of Search ............................... 600/300, 301, 600/485, 493–6, 500–503, 504, 529, 549, 561, 587, 595

(56) References Cited

U.S. PATENT DOCUMENTS 5,215,097 A * 6/1993 Watabe ........................ 600/502
5,447,167 A * 9/1995 Fleischaker .................. 600/595
5,964,720 A * 10/1999 Pelz ............................ 600/595

* cited by examiner

Primary Examiner—Robert L. Nasser
(74) Attorney, Agent, or Firm—Pennie & Edmonds LLP

(57) ABSTRACT

The present invention relates to a writing brush or instrument that can be used to enhance general health and render therapeutic effects in treating behaviourial, psychological, mental and psychosomatic disorders. The writing instrument has one or more biological detectors embedded in or attached to the shaft of the writing brush or instrument. The biological detectors record the biological activities of the user that are associated with the user's sensory, perceptual, emotional, cognitive and physiological conditions during writing or drawing. Sensory signals from the detectors can provide ongoing information of the user's graphonomic act and thus enable the user to control and regulate his or her bodily conditions throughout the writing process by influencing the changes in the sensory signals. The present invention is capable of improving the user's general health as well as providing therapeutic treatment for users with physical or mental disorders.

17 Claims, 4 Drawing Sheets

BRUSH-WRITING INSTRUMENTS FOR HEALTH AND THERAPY

FIELDS OF THE INVENTION

The present invention relates to the fields of behaviourial medicine, psychosomatic medicine, psychiatry, rehabilitation, special education, and clinical and health psychology. In particular, the present invention relates to a handwriting instrument for self-regulating bodily activities associated with the handwriting act.

BACKGROUND OF THE INVENTION

Chinese calligraphy is a traditional Chinese art with a history of several thousand years and is practiced by millions of people in Asia today. Psychological research in the past twenty years has established that this ancient art is capable of achieving, in the course of its execution, emotional stabilization, mental relaxation and physiological slowdown, from the physical perspectives. From the standpoint of the cognitive activities, studies have confirmed its positive impact on heightened attention and concentration, enhanced problem-solving capabilities of spatial abilities, spatial and abstract reasoning as well as quicker response time and improved short-term memory. These original findings by the author have led to the establishment of a brush calligraphic training as an effective technique of intervention of a number of psychosomatic, behaviourial and psychological disorders. These include essential hypertension, type II diabetes, emotional conditions in mental patients, as well as attentional and behaviourial enhancement in children with attention deficit and hyperactivity (ADHD) and mild mental retardation.

For the general population, these changes associated with brush-writing have been found to be capable of enhancing their general health condition. Our recent research has also confirmed that the brush-writing effects are not confined to writing Chinese characters. Similar effects are found when the writing act involved English letters and words and other visual forms. These observations help to substantiate the notion that the beneficial functions of brush handwriting (BHW) go beyond linguistic barriers between writing systems but are general and universal. This lays the foundation for developing instruments of brush handwriting, for health improvement, and therapeutic and rehabilitative intervention, that will have global significance and application. The overall findings have confirmed the efficacy of a psychomeometric system of BHW as a general system of constructive behavior regulation and change. This system specifies the types and styles of Chinese characters or other visual forms, sequencing of the styles and forms, duration of training, size and configurations of the brush, the geometricity of characters or spatial forms etc. on the basis of a theoretical framework developed by the author.

Biofeedback training (BFT) refers to clinical training procedures used to modify physiological responses or patterns of such responses that aim to achieve self-regulation of maladaptive responses and disordered states. It includes a set of procedures that enable the individual to control certain specified physiological processes by providing an external cue or monitor to indicate the activity of that process. Biofeedback represents the prototypical approach of the discipline of "behaviourial medicine." Within behavioral medicine, biofeedback is one clinical technique among many others, which have been introduced as interventions for health disorders. The principles of biofeedback have also been applied in the design of products and instruments used for ordinary practice and training by normal individuals.

When applied to people without obvious health disorders, biofeedback can enhance self-regulation of bodily processes to improve general health such as the generation of specific patterns of brain waves in the practice of transcendental meditation. This technique offers an effective process of treating illnesses as well as enhancing the health of the people under a system of feedback regulation of bodily states.

The present invention together with its variations included in this application integrates the two effective systems, the BHW and the BFT, into a powerful biofeedback device for self-regulation of the brush handwriting process for the purpose of health and clinical intervention.

SUMMARY OF THE INVENTION

The present invention integrates the principles of the biofeedback training (BFT) system with those of the Chinese brush handwriting (BHW) system into a powerful biomedical writing instrument for self-regulation of bodily activities associated with the handwriting act. The present invention comprises a conventional Chinese writing brush with a built-in physiological monitoring and sensing device embedded in the shank of the brush. In addition, a sensory feedback display device is included and embedded in the brush to display the changes in the sensory activities of the user in the course of handwriting through specified sensory signals. Alternatively, the monitoring may be conducted through external sensing devices such as a strap or a ring, which is attached to the writing brush, depending upon the type of feedback required of the practitioner.

The biofeedback display consists of sensory signals, e.g., visual, auditory or thermal, about the current state of the user's bodily conditions, which reflect states of the user's behavioral, mental, and physiological changes during brush writing or drawing. Feedback signals may be based on singular or multiple sensory modalities and will enable the practitioner to effect changes in the signals through conscious control of the brush-writing process.

The specific functions of the present invention serve four specific behavioral dimensions of the practitioners, i.e., the general health (HQ), emotional stabilization (EQ), cognitive activation (IQ) and muscular control efficiency (MQ). Different biofeedback mechanism will be employed for each of the dimensions identified.

The HQ Brush is the instrument which will display biofeedback of bodily conditions helpful for the promotion of general health. The HQ brush has two versions of sensory detection and feedback display in the form of an embedded or external sensing device linked to the brush. It has the option of a visual (color), auditory (tone), or thermal (skin temperature) display of feedback information. The biological index to be measured in the course of handwriting can be in one or more of the following three available sources: the heart rate (HR), the blood pressure (BP) or the pulse rate (PR).

The EQ Brush is the instrument which will display biofeedback of bodily conditions helpful for the enhancement of emotional stability, reduction of anxiety and positive increase of mood conditions. The EQ brush has two versions of sensory detection and feedback display in the form of an embedded or external sensing device linked to the brush. It has the option of a visual (color), auditory (tone) or thermal (skin temperature) display of the feedback information. The biological index to be measured in the course of handwriting can be one of more of the following three available sources: the digital pulse volume (DPV), the galvanic skin response (GSR), or skin temperature (ST).

The IQ Brush is the instrument, which will monitor states of specific and selected patterns of EEG activities of the user during the writing process. The selected brain wave patterns are reflections of higher states of cognitive functioning associated with creativity, memory, attention, and problem solving. This brush will have only external sensing devices linked to the writing brush for monitoring of the states of EEG changes. It has the option of visual (color), auditory (tone) or thermal (skin temperature) display of the feedback information.

The MQ Brush is the instrument which will display conditions of the user's motoric or muscular control of the writing act as feedback in order to enable the user to conduct proper or corrective manipulative and transport movements for efficient drawing or handwriting tasks. The sources of the biofeedback are derived from the motor activities of the user relative to certain practical conventions or behavioral criteria that are associated with good penmanship. This instrument aids and helps the learning, training as well as corrective or rehabilitative remediation for good penmanship and graphic skills.

Each type of biofeedback-based brush described above renders the most effective health and therapeutic functions when it is integrated with the principles of Chinese brush handwriting system into a comprehensive Biofeedback Brush-writing Training System (BBTS). Special packages of the training can be designed to target at specified category of health conditions or illnesses in question. In the present application, an exemplary set often (10) designs of the invention is put forward to demonstrate the innovative merits of the inventions as well as its potential for the development of further designs within this general conceptual framework of the biofeedback based handwriting and instrument design for the enhancement of health and therapy.

BRIEF DESCRIPTION OF THE DRAWINGS

These and other features, aspects, and advantages of the present invention will become much more apparent from the following description, appended claims, and accompanying drawings, in which:

DETAILED DESCRIPTION OF THE PREFERRED EMBODIMENTS

Figure 1A:
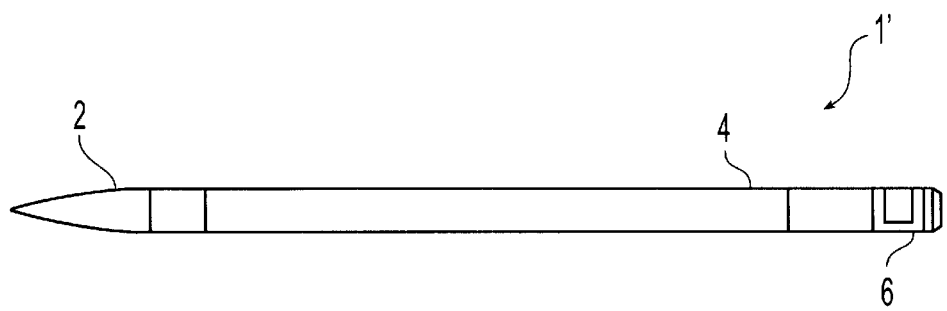
FIG. 1a shows a prior art writing instrument.

Various writing instruments embodying the principles of the present invention are illustrated in FIGS. 1b to 11. The writing instrument of the present invention are capable of self-regulating bodily activities associated with the handwriting act. In each embodiment, the same elements are designated with reference numerals having the same last digits and repetitive descriptions are omitted.

The features of the present invention may be better understood through the following description of an exemplary prior art as shown in FIG. 1a. It shows the typical configuration of a conventional soft tip writing instrument 1 having standard components of a soft writing tip 2, a writing shaft 4 and a tail-cap 6 of a conventional brush. The physical characteristics of the writing instrument 1, such as stiffness, size, weight, diameter, may vary from one model to another, as is the case with these brushes on the market.

Figure 1B:
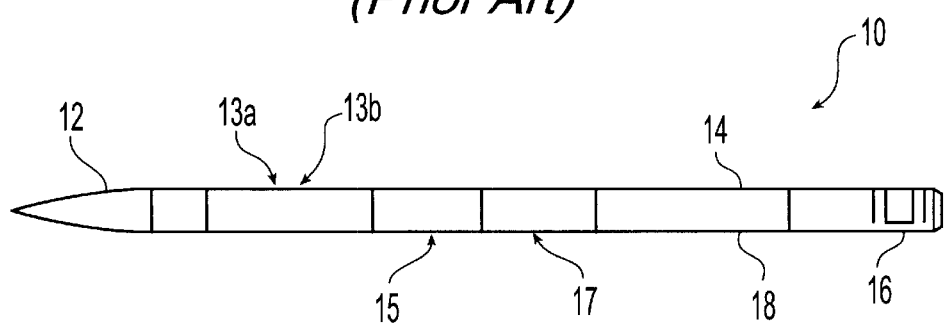
FIG. 1b shows a writing instrument of the present invention with key components including embedded and external bio-sensors, feedback mechanism, feedback display unit and power unit.

FIG. 1b shows a writing instrument 10 of the present invention in the form of a soft tip brush. The novel components of the present invention comprise a bio-sensing unit 13, a sensory feedback mechanism 15, a feedback display unit 17 and a power supply unit 18. The components 13, 15, 17 and 18 can be embedded in or external to the shaft 14.

The bio-sensing unit 13 may be a bio-sensor 13a embedded in the shaft 14 or a bio-sensor 13b externally linked through wires to the shaft 14, depending on the brush type. In a preferred embodiment, the bio-sensing units 13 are electrodes. The bio-sensing unit 13 measures one or more of the many available physiological indices from the user during the writing act. The available indices include EEG, EMG, GSR, Heart rate (HR), blood pressure (BP), digital pulse volume (DPV), skin temperature (ST), and pulse rate. The adoption of any of the indices in a given brush depends upon the functions to be served by the particular brush design.

The biofeedback mechanism 15 transmits the captured physiological indices to the biofeedback display unit 17. The biofeedback display unit 17 displays the biological signal from the user back to the user. The display is conducted through one of the three sensory modalities: the visual, auditory or thermal signals. The visual signals may be displayed in the form of color codes in singular or multiple colors, the auditory signals can be displayed by a tonal code and the thermal signals by skin temperature.

The power unit 18 in each brush 1 enables the operation of the bio-sensing unit 13 as well as the feedback mechanism 15 and the feedback display mechanism 17. The power unit 18 involves the installation of suitable micro batteries.

The First Basic Embodiment

Figure 2:
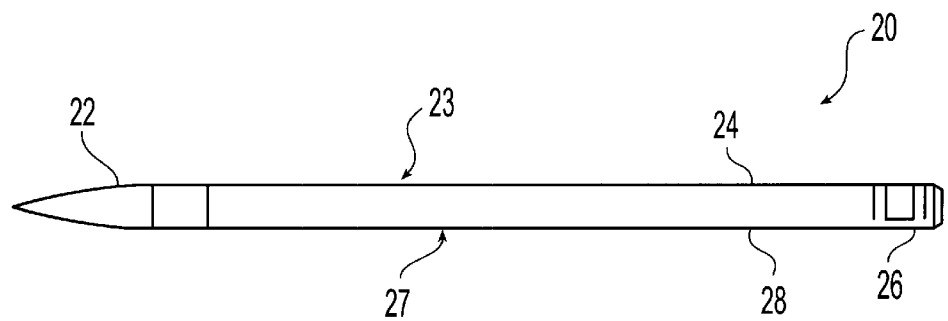
FIG. 2 is a basic embodiment of the HQ1 (general health) brush of the present invention with embedded bio-sensing electrode.

FIG. 2 shows the basic embodiment of the HQ1 Brush (General Health) 20 of the present invention. In addition to the conventional components as shown in FIG. 1a, this embodiment comprises three novel, technical components: a bio-sensing unit 23, a biofeedback display unit 27 and a power unit 28. The bio-sensing unit 23 is preferred to be a built-in bio-sensors 23a embedded in the brush shaft 24. The bio-sensing unit 23 may be one of the three bio-sensors for sensing and measuring heart rate, blood pressure and pulse rate, respectively, making altogether three models of the HQ1 Brush. Additional new sensors for the detection of other physiological states or combination of two or more existing bio-sensors 23 can create additional models of the HQ1 Brush.

The biofeedback display unit 27 for any of the HQ1 Brush models 20 comprises the option of visual, auditory or thermal signals to be installed singularly or in combination. The visual feedback will use color codes, e.g., yellow, amber, and green, to reflect the extent of the physiological changes in a continuously changing mode. In alternative, the visual feedback can be displayed by the intensity or dimming of colored light indicator or other optional visual display mechanisms. The auditory feedback will employ an audible tone with free-flow up-down configuration, or its variations. The thermal display will take the form of continuous thermal signals varying in temperature from the brush shaft 24 in a continuous changing and up-down mode.

Moreover, the power unit 28 for the HQ1 Brush 20 comprises the latest technology in microelectronics. The tiniest possible power cells will be adopted for operating the sensing unit 23 and the display mechanisms 27 of the brush 20. Finally, the physical features of the HQ1 Brush 20, such as weight, size, shaft length, and surface texture, will be determined and depend upon the composition of component parts and associated design considerations.

The Second Basic Embodiment

Figure 3:
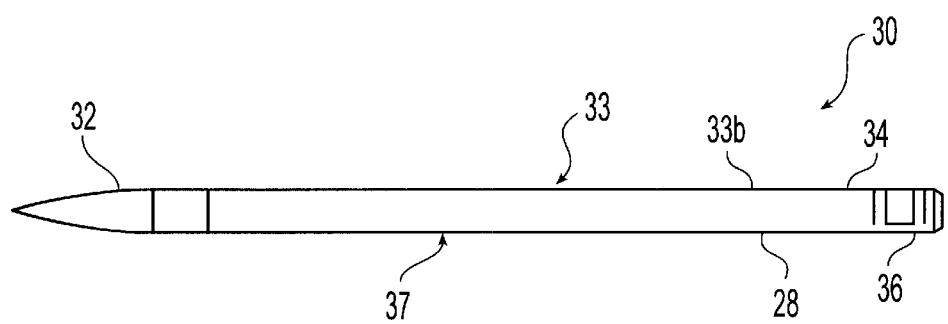
FIG. 3 is a basic embodiment of the HQ2 (general health) brush of the present invention with external bio-sensing electrode.

FIG. 3 shows the HQ2 Brush (general health) 30 of the present invention. The structural details of brush 30 are the same to those of brush 20 except that the sensing device 33 are externally linked to the brush 30, instead of embedded in the brush shaft 34. This external sensing device 33b allows more flexible application of sensing electrodes to measure bio-indicators, such as HR, BP or pulse rate. In a preferred embodiment, the sensing device 33 can be a finger strap 33b with electrode, or a set of electrodes (not shown) which can be attached to relevant parts of the body for more sophisticated users. The external sensing device 33b may also be integrated with larger or more advanced biological recording system for more varied display of biofeedback for the BHW training.

The Third Basic Embodiment

Figure 4:
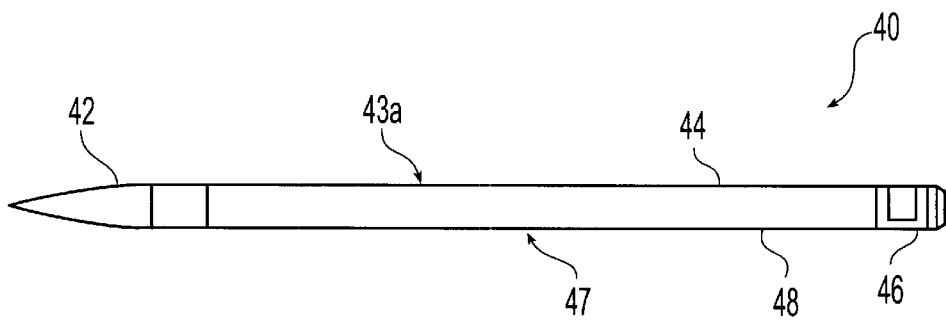
FIG. 4 is a basic embodiment of the EQ1 (emotional health) brush of the present invention with embedded bio-sensing electrodes.

FIG. 4 shows an embodiment of the EQ1 Brush (emotional health) 40 of the present invention. In addition to the conventional components, brush 40 has a sensing unit 43, a feedback display unit 47 and a power unit 48. The sensing unit 43 preferably has built-in electrodes 43a and can measure biological indices reflecting a user's emotion state. In particular, the sensing unit 43 can measure the digital pulse volume (DPV), the skin conductance (GSR) and the skin temperature (ST), respectively, making altogether three separate models of the EQ1 Brush 40. Additional new modes for measuring physiological states or combination of the existing modes will create more models of the brush 40.

The feedback display unit 47 for the EQ1 Brush 40 can be in one of the three available modes of presentation, i.e., visual, auditory or thermal display. The visual display is in the form of color coding (yellow, amber, red, flashing light), the auditory display in the form of audible tone, and the thermal display in the form of varying temperature to the touch. The power unit 48 will be the same as that described in the first basic embodiment.

The Fourth Basic Embodiment

Figure 5:
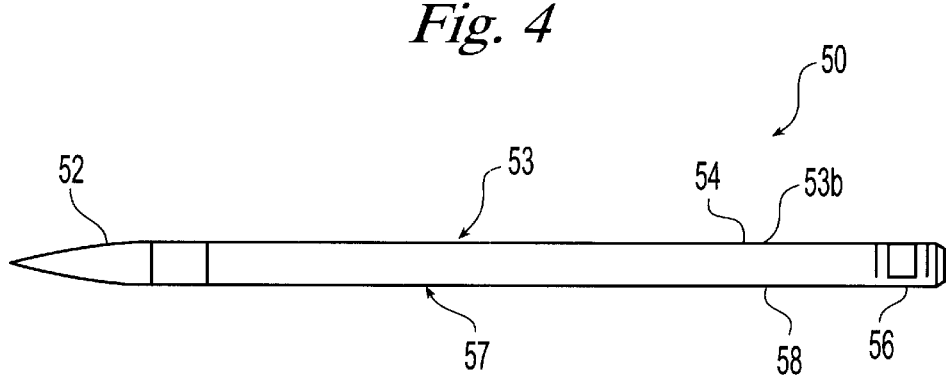
FIG. 5 is a basic embodiment of the EQ2 (emotional health) brush of the present invention with external bio-sensing electrode.

FIG. 5 shows the fourth basic embodiment of the present invention, the EQ2 (emotional health) Brush 50, as a variation of the third basic embodiment. The only difference of this version involves the external linkage of the sensing unit 53. The sensing unit 53 is in the form of a finger strap 53b or a set of electrodes (not shown) for detecting sensory signals from the practicing brush-writing individual. In addition to the three modes of bio-sensory measurement discussed above, the external detachment of the sensing electrodes will allow more flexible use of other sensory modalities in addition to the DPV, GSR, and ST, such as skin conductance (SC), heart rate (HR). This external sensing unit 53b will also be available to link to large polygraphic recording equipment for more sophisticated sensing and monitoring requirements on bodily changes during the brush-writing act.

The Fifth Basic Embodiment

Figure 6:
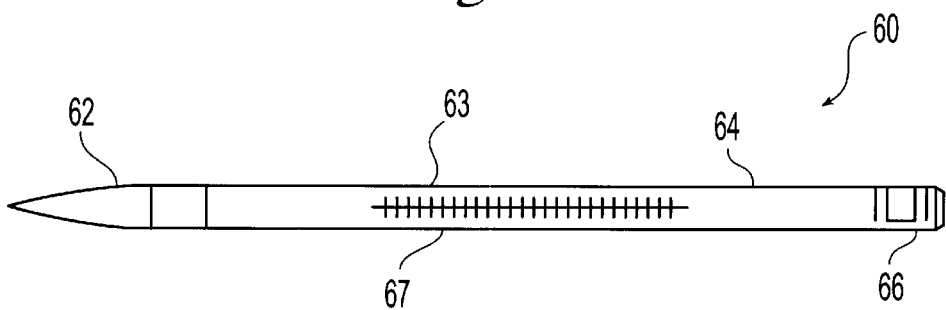
FIG. 6 is a basic embodiment of the EQ3 (emotional health) brush of the present invention with embedded thermometric sensor and display.

FIG. 6 shows a fifth basic embodiment of the present invention, the EQ3 (emotional health) Brush 60. According to this embodiment, the sensing unit 63 is a thermometric detector 63a. In a preferred embodiment, the thermometric detector 63a is embedded in the brush shaft 64 for recording the changes of skin temperature of the practitioner during brush-writing.

The display unit 67 of brush 60 displays the user's body temperature in the form of an analog or digital signals as two separate models. The display unit 67 is preferred to be embedded in the brush shaft 64. In a preferred embodiment, the thermometric detector 63 and the display unit 67 are combined to carry out the sensing and displaying functions, similar to a thermometer. Accordingly, the brush 60 is capable of using any readily available thermometric devices, instead of color codes for visual display as in the EQ1 and EQ2 brushes 40 and 50.

The Sixth Basic Embodiment

Figure 7:
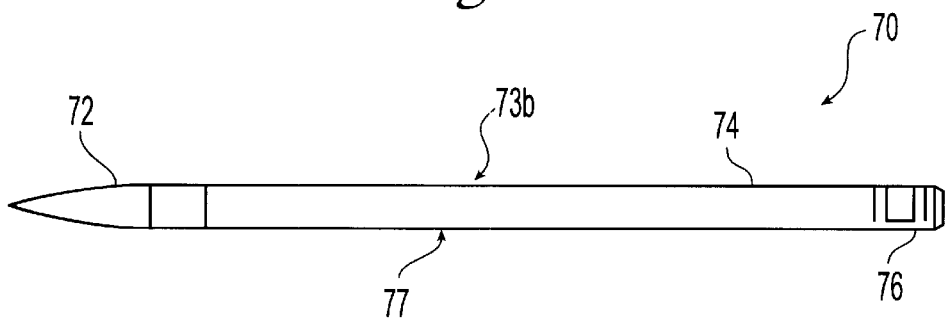
FIG. 7 is a basic embodiment of the CQ1 (cognitive health) brush of the present invention with external bio-sensing electrode for brain waves.

FIG. 7 shows the six basic embodiment of the present invention, the CQ (cognitive health) Brush 70. This brush 70 measures mainly the EEG activities of the brain in order to reflect the various states of cognition associated with the act of brush-writing. Since different sites of the cortex are responsible for different dimensions of behavior, the selected sites will be linked externally as well as singularly to the brush 70. Thereby, the EEG signals from a given site will become the feedback data relayed back to the user for BHW training purposes. Common sites in connection with human cognitive activities include P3, P4, C3, C4, T3, T4, where different patterns of the brain waves will reflect different cognitive functions. Beta waves are found to relate to the active alertness and arousal, while alpha waves reflect a state of the mind with the most creative cognitive outcomes take place.

The sensing unit 73 can be single wave electrode 73b that is externally linked to the brush shaft 74. Single wave electrode measurement is available so that specific functions served by the wave pattern become the source for feedback information. The single wave electrode forms the external basis of a given model of the brush 70. There can be as many models of the brush 70 as there is the variety of wave patterns associated with the cognitive functions. This system may be attached to a multi-channel polygraph recorder for more advanced feedback training with this special CQ brush.

The display unit 77 may use color-coding (yellow, amber, red, or flashing light), auditory signal of an up-down tone, or thermal signals as discussed above.

The Seventh Basic Embodiment

Figure 8:
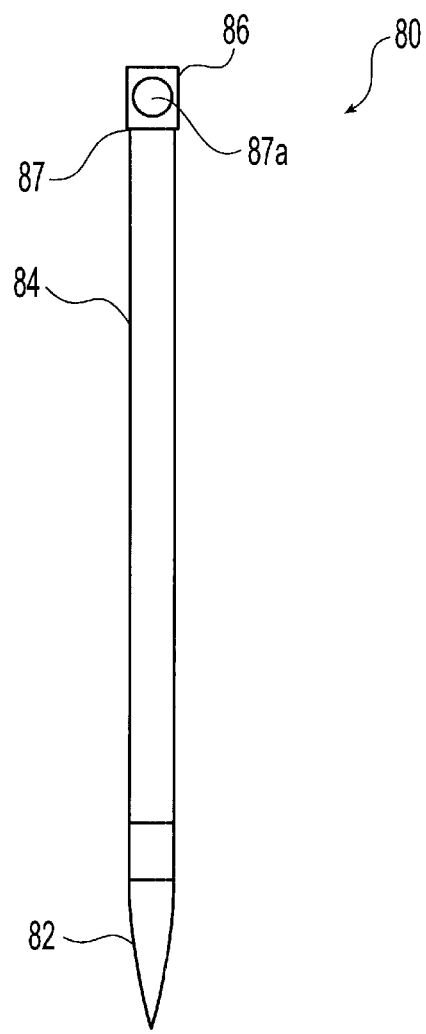
FIG. 8 is a basic embodiment of the MQ1 (motor efficiency) brush or a hard-tip pen of the present invention with an embedded spirit-level gauge in the shaft.

FIG. 8 shows the seventh basic embodiment of the present invention, the MQ1 (motor efficiency) brush 80. In this embodiment, the brush 80 can comprise a sensing device 87, such as a spirit-level gauge 87. The essence of this design lies in the use of the spirit-level gauge 87 as a display device, such as a feedback unit. The spirit-level gauge 87 is preferably embedded in the brush shaft 84 and mounted on the opposite end of the tip 82. The spirit-level gauge 87 displays visual feedback information regarding the degree of motor control efficiency of the user with reference to the verticality of the brush relative to the writing surface.

The ability to maintain vertical position of the writing instrument is one essential component to the attainment of attention and facilitation of task concentration. For the BHW especially, this rigid motor control is essential in the traditional calligraphic training, which is also closely linked to the elevation of emotional stability.

In a preferred embodiment, the spirit-level gauge 87 includes a sealed bubble 87a which by its very nature will indicate the extent of the vertical alignment of brush 80 relative to the writing surface. In a more preferred embodiment, the bubble can be color-coded for an easy recognition and monitoring during the writing process.

The Eighth Basic Embodiment

Figure 9:
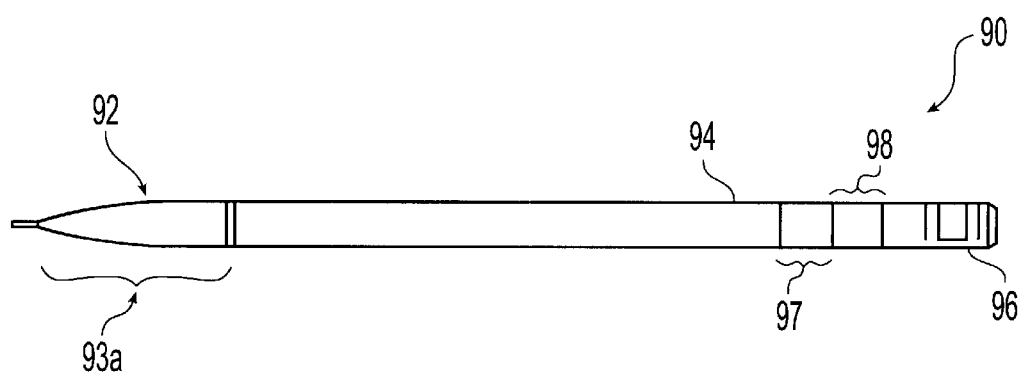
FIG. 9 is a basic embodiment of the MQ2 (motor efficiency) hard-tip writing instrument of the present invention with embedded pressure transducers for the tip of the pen.

FIG. 9 shows the eighth basic embodiment of the present invention, the MQ2 (motor efficiency) hard-tip pen 90. The pen comprises an embedded pressure transducer 93a in the lower section of the pen shaft 94, which responds to the pressure exerted to the lower portion of the pen 94 by the user. In an exemplary embodiment, the pressure transducer 93a can respond to the pressure that the user exerts on the tip of the hard-tip pen 90 during the writing or drawing activity. Additionally or alternatively, the pressure transducer 93a can sense the kinesthetic information of the tip movement. This pressure and/or kinesthetic information is recorded by the transducer 93a and fed back and displayed in visual or auditory signals. For the visual displays, it can be color-coded lights in three discrete modes, and for auditory signal, in the form of a continuous tone varying in pitch or discrete tones showing three levels of the sound in order to reflect the tip pressure.

The writing instrument 90 according to this embodiment is mainly designed for the use with a hard-tip writing instrument, in which the tip pressure is easily measured by the transducer 93a. However, the design can also be applied to a brush which contains a relatively stiff soft-tip. The spirit of this embodiment is to caution the user of the excessive force exerted onto the shaft 94, and to prevent the development of callous on the user's hand and fingers due to sustained exertion of force in the course of the writing act.

The Ninth Basic Embodiment

Figure 10:
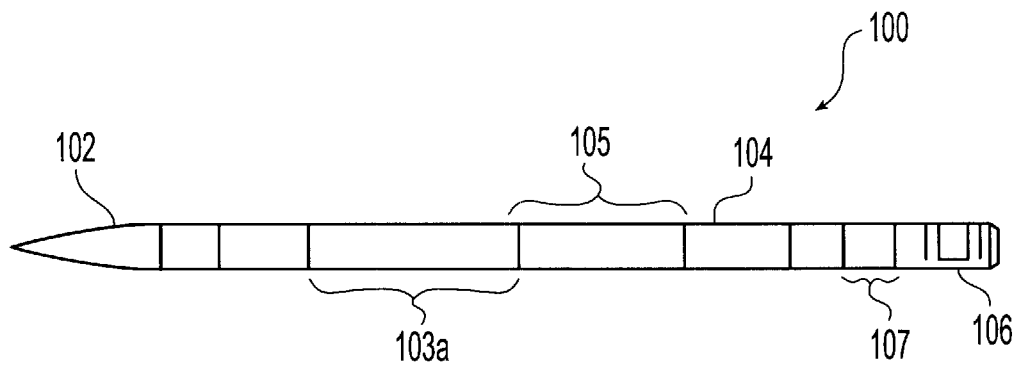
FIG. 10 is a basic embodiment of the MQ3 (motor efficiency) hard-tip writing instrument of the present invention with embedded pressure transducers for the shaft of the pen.

FIG. 10 shows the ninth basic embodiment of the present invention, the MQ3 (motor efficiency) pen 100. The writing instrument 100 comprises pressure transducers embedded in the shaft 104 for sensing and monitoring the pressure exerted on the shaft 104 by the user in the course of writing. This design helps to alert the user of any excessive force the user may generate while writing and to caution the user to reduce the excessive pressure so as to decrease muscular fatigue caused by writing. Moreover, it helps to prevent callous and cramps from developing in the user's fingers and hand.

The feedback display unit 107 generates feedback signals in relation to the user's control force. The feedback signals can be displayed visually or auditorily. For visual display, the feedback signals may be color-coded in three modes of light or one color-code with differing light intensity for the same purpose. For auditory displays of pressure, the feedback signals can be in the form of a constant tone in three levels of the pitch, or one continuous tone with rising and falling pitch sound to reflect the magnitude of the force exertion on the instrument by the user.

The Tenth Basic Embodiment

Figure 11:
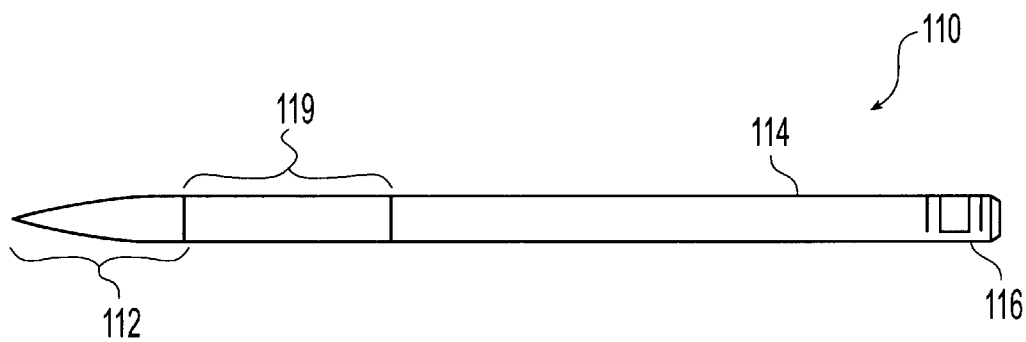
FIG. 11 is a basic embodiment of the MQ4 (motor efficiency) pen of the present invention with retractable tip unit.

FIG. 11 shows the tenth basic embodiment of the present invention, the MQ4 (motor efficiency) pen 110. The basic idea of this embodiment is to produce 3-D or 3-D like movement from a hard-tip writing instrument 110 so that it will write like a soft-tip brush. Ultimately, the user will be able to enjoy many of behavioral benefits in the user's cognitive, emotional, perceptual, motor and physiological changes from writing with such a writing instrument 110.

The retractable property of a hard-tip can be achieved by using a retractable mechanism 119. The retractable mechanism 119 is preferred to be embedded in the shaft 114 just above the tip 112 of the writing instrument 110. The retraction magnitude of the tip 112 depends on the elasticity degree of the tip 112 desired. In a preferred embodiment, the retractable mechanism 119 has plural grades of such elasticity. The feedback provided to the user regarding the elasticity level can be just the natural kinesthetic information from the movement of the tip 112 and the pen 110, without the need for further elaboration of visual or auditory displays. The embodiment may incorporate some of the design features of the first ten basic embodiments as described above.

What is claimed is:

1. A writing instrument for providing biofeedback training to a user during the user's writing act, comprising:
   a writing shaft having a soft tip;
   a sensing device for sensing and recording a sensory signal of the user, the sensory signal being selected from the group consisting of heart rate, EEG, EMG, GSR, respiration, blood pressure, skin conductance, skin temperature, digital pulse volume, and pulse rate; and
   a display device for showing conditions and changes of the user's physiological states reflected by the sensory signal detected during the writing act to provide a feedback to the user for self-regulating physiological behavior;
   wherein the sensing device and the display device are externally linked to electronic monitoring and display systems.

2. The writing instrument of claim 1, wherein the writing instrument is a Chinese writing brush.

3. The writing instrument of claim 1 further comprising a power unit embedded in the writing shaft,
   wherein the sensing device is a bio-sensing device, and
   wherein the display device is a biofeedback display device.

4. The writing instrument of claim 3, wherein the power unit comprises micro batteries.

5. The writing instrument of claim 1, wherein the sensing device and the display device are embedded in the writing shaft.

6. The writing instrument of claim 1, wherein the sensing device and the display device are externally linked to polygraph recording equipment or computer system with a monitor.

7. The writing instrument of claim 1, wherein the sensing device comprises a pressure transducer embedded in the writing shaft to monitor the force exerted thereon by the user during the writing activity.

8. The writing instrument of claim 1, wherein the display device generates a signal selected from the group consisting of visual, auditory, tactile, and thermal signals.

9. The writing instrument of claim 1, wherein the display device is a visual display device, which generates color-coded lights in plural discrete light modes.

10. The writing instrument of claim 1, wherein the display device is an auditory display device, which generates a continuous tone with plural pitch levels or discrete tones of varying sound levels.

11. The writing instrument of claim 1 further comprising a retractable mechanism capable of retracting the writing tip into the writing shaft.

12. The writing instrument of claim 1, wherein the writing act is conducted in 1D, 2D or 3D space.

13. A writing instrument for providing biofeedback training to a user during the user's writing act, comprising:

a writing shaft having a soft tip;

a sensing device for sensing and recording a sensory signal of the user, the sensory signal being selected from the group consisting of heart rate, EEG, EMG, GSR, respiration, blood pressure, skin conductance, skin temperature, digital pulse volume, and pulse rate; and a display device for showing conditions and changes of the user's physiological states reflected by the sensory signal detected during the writing act to provide a feedback to the user for self-regulating physiological behavior;

wherein the sensing device senses and records a plurality of sensory signals of the user.

14. A writing instrument for providing biofeedback training to a user during the user's writing activity, comprising:

a writing shaft;

a sensing device for sensing and recording the user's sensory signal;

a display device for showing conditions and changes of the user's physiological states during the writing activity; and a power unit embedded in the writing shaft;

wherein the sensing device and the display device are integrated as a sealed bubble gauge.

15. The writing instrument of claim 14, wherein the sensory signal is selected from the group consisting of HR, EEG, EMG, GSR, BP, skin conductance, skin temperature, respiration, digital pulse volume, and pulse rate.

16. The writing instrument of claim 14, wherein at least one of the sensing device, the display device, and the power source is externally linked to the writing shaft of the writing instrument.

17. A writing instrument for providing biofeedback training to a user during the user's writing activity, comprising:

a writing shaft having a writing tip;

a sensing device for sensing and recording the user's sensory signal;

a display device for showing conditions and changes of the user's physiological states during the writing activity; and a power unit embedded in the writing shaft;

wherein the display device shows the kinesthetic information of the writing tip movement.

* * * * *